United States Patent
Cook et al.

(10) Patent No.: US 11,344,449 B2
(45) Date of Patent: May 31, 2022

(54) THERMALLY ROBUST LASER PROBE ASSEMBLY

(71) Applicant: Novartis AG, Basel (CH)

(72) Inventors: Christopher Cook, Laguna Niguel, CA (US); Chenguang Diao, Irvine, CA (US); Mark Harrison Farley, Laguna Hills, CA (US); Alireza Mirsepassi, Irvine, CA (US); Kambiz Parto, Laguna Niguel, CA (US); Ronald T. Smith, Irvine, CA (US)

(73) Assignee: Alcon Inc., Fribourg (CH)

( * ) Notice: Subject to any disclaimer, the term of this patent is extended or adjusted under 35 U.S.C. 154(b) by 91 days.

(21) Appl. No.: 16/218,382

(22) Filed: Dec. 12, 2018

(65) Prior Publication Data

US 2019/0175273 A1  Jun. 13, 2019

Related U.S. Application Data

(60) Provisional application No. 62/630,865, filed on Feb. 15, 2018, provisional application No. 62/622,299, (Continued)

(51) Int. Cl.
*A61F 9/00* (2006.01)
*A61F 9/008* (2006.01)
(Continued)

(52) U.S. Cl.
CPC .......... *A61F 9/00821* (2013.01); *A61B 18/22* (2013.01); *A61B 18/24* (2013.01);
(Continued)

(58) Field of Classification Search
CPC ..................................................... A61B 18/22
See application file for complete search history.

(56) References Cited

U.S. PATENT DOCUMENTS 4,632,505 A * 12/1986 Allsworth ................ G02B 6/32
                                                              385/61
5,199,431 A    4/1993 Kittrell
(Continued)

FOREIGN PATENT DOCUMENTS

JP    A1994014936 A    1/1994
JP    2013048864 A     3/2013
(Continued)

OTHER PUBLICATIONS

Biron, Michel. Thermoplastic and Thermoplastic Composites. 2nd ed., William Andrew Publishing, 2013, https://www.sciencedirect.com/topics/materials-science/refractive-index (Year: 2013).*
(Continued)

*Primary Examiner* — Gary Jackson
*Assistant Examiner* — Anant A Gupta

(57) ABSTRACT

Certain aspects of the present disclosure provide a thermally robust laser probe assembly comprising a cannula, wherein one or more optical fibers extend at least partially through the cannula for transmitting laser light from a laser source to a target location. The probe assembly further comprises a lens housed in the cannula and a protective component press-fitted to the distal end of the cannula, wherein the lens is positioned between the one or more optical fibers and the protective component.

20 Claims, 4 Drawing Sheets

Related U.S. Application Data filed on Jan. 26, 2018, provisional application No. 62/598,653, filed on Dec. 14, 2017, provisional application No. 62/597,550, filed on Dec. 12, 2017.

(51) Int. Cl.

| | | |
|---|---|---|
| *A61B 18/22* | (2006.01) | |
| *G02B 6/38* | (2006.01) | |
| *A61B 90/30* | (2016.01) | |
| *A61B 18/24* | (2006.01) | |
| *G02B 6/02* | (2006.01) | |
| *G02B 6/42* | (2006.01) | |
| *A61B 18/00* | (2006.01) | |
| *A61B 18/20* | (2006.01) | |

(52) U.S. Cl.
CPC .............. *A61B 90/30* (2016.02); *A61F 9/008* (2013.01); *A61F 9/00823* (2013.01); *G02B 6/3843* (2013.01); *G02B 6/3851* (2013.01); *G02B 6/3885* (2013.01); *A61B 2018/00779* (2013.01); *A61B 2018/208* (2013.01); *A61B 2018/2025* (2013.01); *A61B 2018/2065* (2013.01); *A61B 2018/2211* (2013.01); *A61B 2018/2255* (2013.01); *A61B 2018/2266* (2013.01); *A61B 2018/2294* (2013.01); *A61B 2090/306* (2016.02); *A61F 2009/00863* (2013.01); *G02B 6/02042* (2013.01); *G02B 6/4206* (2013.01)

(56) References Cited

U.S. PATENT DOCUMENTS

| | | |
|---|---|---|
| 5,496,305 A | 3/1996 | Kittrell |
| 5,625,638 A | 4/1997 | Trost |
| 5,693,043 A | 12/1997 | Kittrell |
| 5,921,981 A | 7/1999 | Bahmanyar et al. |
| 6,066,128 A | 5/2000 | Bahmanyar et al. |
| 6,096,028 A | 8/2000 | Bahmanyar et al. |
| 6,893,432 B2 | 5/2005 | Intintoli et al. |
| 7,189,226 B2 | 3/2007 | Auld et al. |
| 7,302,142 B2 | 11/2007 | Conde |
| 7,448,995 B2 | 11/2008 | Wiklof |
| 7,566,173 B2 | 7/2009 | Auld et al. |
| 8,398,240 B2 | 3/2013 | Smith |
| 8,488,930 B2 | 7/2013 | Papac |
| 8,498,506 B2 | 7/2013 | Smith |
| 8,561,280 B2 | 10/2013 | Diao et al. |
| 8,571,364 B2 | 10/2013 | Smith |
| 8,764,261 B2 | 7/2014 | Smith |
| 8,903,475 B2 | 12/2014 | Brennan et al. |
| 8,939,964 B2 | 1/2015 | Smith |
| 8,951,244 B2 | 2/2015 | Smith |
| 8,968,347 B2 | 3/2015 | McCollam |
| 9,055,885 B2 | 6/2015 | Horvath |
| 9,107,730 B2 | 8/2015 | Huculak et al. |
| 9,211,214 B2 | 12/2015 | Rubinchik |
| 9,308,128 B2 | 4/2016 | Smith |
| 9,364,982 B2 | 6/2016 | Schaller |
| 9,387,040 B2 | 7/2016 | Smith |
| 9,402,643 B2 | 8/2016 | Auld |
| 9,681,793 B2 | 6/2017 | Artsyukhovich |
| 10,012,800 B2 | 7/2018 | Diao |
| 10,016,302 B2 | 7/2018 | Shazly |
| 10,111,778 B2 | 10/2018 | Smith |
| 10,245,181 B2 | 4/2019 | Diao |
| 10,433,718 B2 | 10/2019 | Liolios |
| 10,441,157 B2 | 10/2019 | Smith |
| 2002/0045811 A1 | 4/2002 | Kittrell |
| 2002/0193781 A1* | 12/2002 | Loeb ............. A61B 18/1402 606/15 |
| 2004/0120668 A1* | 6/2004 | Loeb .............. A61B 18/22 385/117 |
| 2004/0236183 A1 | 11/2004 | Durell |
| 2006/0184162 A1 | 8/2006 | Smith |
| 2008/0051770 A1 | 2/2008 | Scheller et al. |
| 2008/0177257 A1 | 7/2008 | Smith et al. |
| 2008/0215041 A1 | 9/2008 | Zemmouri |
| 2008/0243108 A1 | 10/2008 | Murakami |
| 2009/0270850 A1 | 10/2009 | Zhou |
| 2009/0287196 A1 | 11/2009 | Zelickson |
| 2009/0287197 A1 | 11/2009 | Hanley |
| 2010/0027943 A1 | 2/2010 | Armani |
| 2010/0261961 A1 | 10/2010 | Scott |
| 2011/0122366 A1 | 5/2011 | Smith |
| 2011/0144627 A1 | 6/2011 | Smith |
| 2012/0022327 A1* | 1/2012 | Baba ............. G02B 13/06 600/109 |
| 2012/0123399 A1* | 5/2012 | Belikov ............ A61B 18/201 606/16 |
| 2012/0191078 A1 | 7/2012 | Yadlowsky |
| 2013/0150839 A1 | 6/2013 | Smith |
| 2013/0178789 A1* | 7/2013 | Mackool ............. A61B 90/37 604/22 |
| 2014/0180264 A1 | 6/2014 | Diao et al. |
| 2014/0194862 A1 | 7/2014 | Smith et al. |
| 2014/0200566 A1* | 7/2014 | Smith ............. A61F 9/00821 606/17 |
| 2014/0250668 A1 | 9/2014 | Smith |
| 2015/0212307 A1* | 7/2015 | Dohi ............. G02B 26/0808 359/385 |
| 2015/0351629 A1 | 12/2015 | Wheatley |
| 2015/0366432 A1 | 12/2015 | Artsyukhovich |
| 2016/0178844 A1* | 6/2016 | Griffin ............... G02B 6/262 385/33 |
| 2016/0299170 A1* | 10/2016 | Ito ..................... A61B 1/00177 |
| 2016/0302868 A1* | 10/2016 | Nagale ............. A61B 18/24 |
| 2018/0055596 A1 | 3/2018 | Johnson |
| 2018/0243136 A1 | 8/2018 | Diao |
| 2018/0243137 A1 | 8/2018 | Diao |
| 2018/0333304 A1 | 11/2018 | Diao |
| 2018/0344528 A1 | 12/2018 | Farley |
| 2019/0142544 A1 | 5/2019 | Horn |
| 2019/0175217 A1 | 6/2019 | Cook |
| 2019/0175300 A1 | 6/2019 | Horn |
| 2019/0175404 A1 | 6/2019 | Cook |
| 2019/0175405 A1 | 6/2019 | Diao |
| 2019/0175406 A1 | 6/2019 | Cook |
| 2019/0175407 A1 | 6/2019 | Bacher |
| 2019/0175408 A1 | 6/2019 | Diao |
| 2019/0209372 A1 | 7/2019 | Farley |
| 2019/0307527 A1 | 10/2019 | Grueebler |
| 2019/0365569 A1 | 12/2019 | Skovgaard |
| 2020/0107960 A1 | 4/2020 | Bacher et al. |

FOREIGN PATENT DOCUMENTS

| | | |
|---|---|---|
| WO | WO9208427 A2 | 9/1992 |
| WO | WO2001037769 A1 | 5/2001 |
| WO | WO2008024848 A2 | 2/2008 |
| WO | WO2018113887 A2 | 6/2018 |

OTHER PUBLICATIONS

Yasuhiro Koike, Yuji Sumi, and Yasuji Ohtsuka, "Spherical gradient-index sphere lens," Appl. Opt. 25, 3356-3363 (1986) (Year: 1986).*

* cited by examiner

US 11,344,449 B2

THERMALLY ROBUST LASER PROBE ASSEMBLY

TECHNICAL FIELD

The present disclosure relates generally to laser probe assemblies and more particularly to such systems used in surgery (e.g., ophthalmic surgery) and the like.

BACKGROUND

A laser probe assembly may be used during a number of different procedures and surgeries. As an example, a laser probe assembly may used during retinal laser surgeries in order to seal retinal tears, among other things. Laser light is typically transmitted from a laser source through an optical fiber cable. The optical fiber cable proximally terminates in a laser connector, which connects to the laser source, and distally terminates in a probe assembly that is manipulated by the surgeon. Note that, herein, a distal end of a component refers to the end that is closer to a patient's body, or where the laser light is emitted out of the laser probe. On the other hand, the proximal end of the component refers to the end that is facing away from the patient's body or in proximity to, for example, the laser source.

The probe assembly comprises a hand-piece coupled to a cannula that is partly inserted in a patient's eye. The optical fiber cable houses an optical fiber that extends through the hand-piece and the cannula to transmit laser light onto the patient's retina. In certain cases, a lens is used to magnify and project the laser beams propagated by the optical fiber on the patient's retina for increased performance. The lens is placed in front of the optical fiber and is attached to the cannula.

In certain cases, the optical fiber cable houses more than one optical fiber, enabling the laser probe assembly to deliver more than one photocoagulation beam at the same time. For example, in certain cases, the optical fiber cable may house four optical fibers or a multi-core optical fiber. In such cases, due to the high power throughput in a confined space (e.g., within the cannula), the cannula and the lens may experience excessive heat when blood or other dark materials exist in front of or at least partially block or touch the tip of the cannula or the lens. In some cases, the excessive heat is created because the laser beams propagated by the optical fibers are reflected back by the blood or the dark material onto the lens, the cannula, and/or the adhesive bonding between the lens and the cannula. This overheating and thermal run-away results in the cannula and the lens melting and also causing the lens to detach from the cannula.

BRIEF SUMMARY

The present disclosure relates to laser probe assemblies and more particularly to such systems used in surgery (e.g., ophthalmic surgery) and the like.

Certain embodiments provide a probe assembly comprising a cannula, wherein one or more optical fibers extend at least partially through the cannula for transmitting laser light from a laser source to a target location. The probe assembly further comprises a lens housed in the cannula and a protective component press-fitted to the distal end of the cannula, wherein the lens is positioned between the one or more optical fibers and the protective component.

Also, certain embodiments provide a surgical system, comprising a laser source, and a probe assembly connected to the laser source through one or more optical fibers. The laser probe assembly comprises a hand-piece connected to a cannula, the cannula comprising a distal end, wherein the one or more optical fibers extend through the hand-piece and at least partially through the cannula for transmitting laser light from the laser source to a target location. The laser probe assembly also comprises a lens housed in the cannula and a protective component press-fitted to the distal end of the cannula, wherein the lens is positioned between the one or more optical fibers and the protective component.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide a probe assembly having a protective component.

As described above, a probe assembly with a high power throughput may experience overheating when blood contaminates the lens or blocks the laser beam such that the lens within the cannula may melt. A melting lens may also detach from the cannula resulting in the probe assembly malfunctioning. Particular embodiments described in the present disclosure may overcome these deficiencies by press-fitting a protective component to the distal end of cannula, wherein the lens is positioned between the one or more optical fibers and the protective component.

Figure 1A:
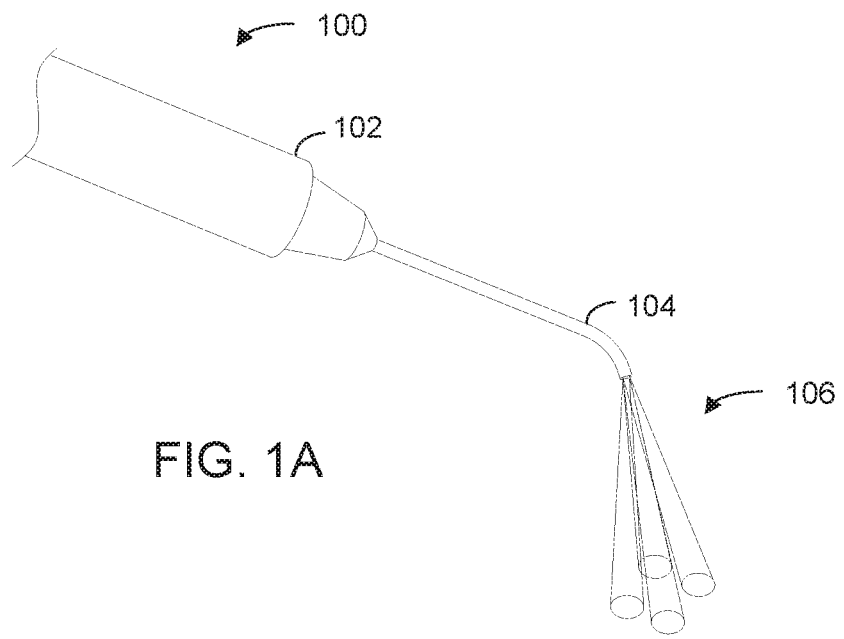
FIG. 1A illustrates an example of a probe assembly comprising a hand-piece and a cannula.

FIG. 1A illustrates an example of a probe assembly 100 comprising a hand-piece 102 and a cannula 104. A surgeon uses hand-piece 102 to guide cannula 104 (e.g., cylindrical shaped hollow tube) into a patient's body part, which may be a patient's eye. As shown, probe assembly 100 concurrently provides multiple photocoagulation beams 106 resulting in multiple laser spots. Each laser spot's power may be between 250-500 milliwatts (mW) such that by providing multiple laser spots, the minimum power passing through cannula 104 may be 1 watt (W). As described above, a lens may be placed in front of the optical fibers, which extend through the cannula, for projecting the laser beams onto, for example, a patient's eye's retinal surface. The proximal end of the optical fibers, as described above, connects to a laser source that is coupled to or part of a surgical system.

Figure 1B:
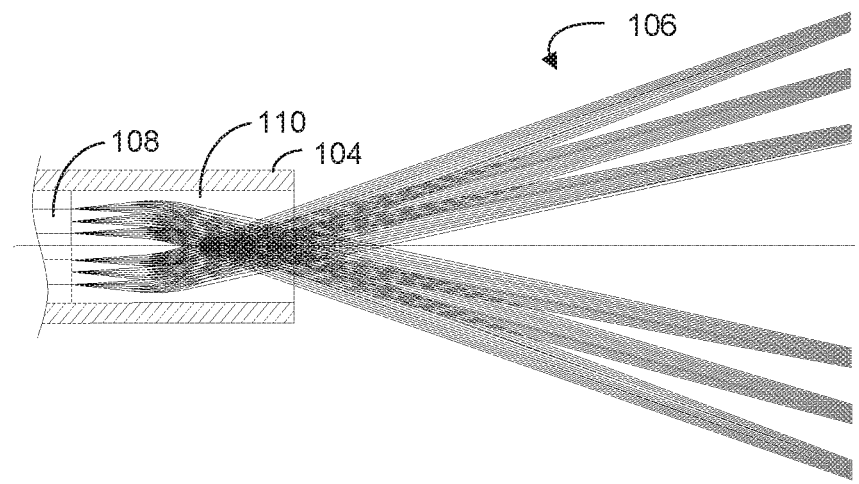
FIG. 1B illustrates a cross-sectional view of the tip of the cannula of FIG. 1A.

FIG. 1B illustrates a cross-sectional view of the tip of cannula 104, where lens 110 is placed for projecting beams 106 propagated by multiple optical fibers 108 extending through cannula 104. Optical fibers 108, in certain aspects, represent an optical fiber array or a multi-core optical fiber. When cannula 104 is placed in a patient's body part, such as through a trocar cannula (not illustrated), beams 106 may be reflected back into cannula 104, such as when there is blood or other dark material in front of the tip of cannula 104 or partially blocking or touching lens 110. The reflection of laser beams back into cannula 104, as well as cannula 104's absorption of such beams, adds to the amount of heat that is already generated within cannula 104. This overheating, as described above, may melt cannula 104 and lens 110 and also cause lens 110 to detach from cannula 104.

Accordingly, the aspects described herein relate to a protective component press-fitted to the distal end of a probe assembly's cannula. The protective component (e.g., protective window) is placed in front of the distal end of a lens that is itself placed in front of one or more optical fibers. The press-fitted protective component protects the lens by restricting movements of the lens along the cannula and/or also by preventing the lens from detaching from the cannula. As the protective component is press-fitted into the distal end of the cannula, it also prevents, minimizes, or at least reduces the amount of fluids (e.g., blood) that may leak (e.g., from the patient's body part) into the cannula during surgery.

Figure 2A:
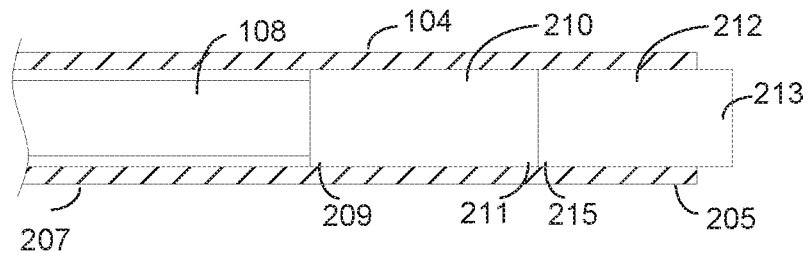
FIG. 2A illustrates a cross-sectional view of an example protective component that is placed at the tip of a cannula, according to some embodiments.

FIG. 2A illustrates a cross-sectional view of an example protective component 212 that is placed at the tip of cannula 104. As shown, protective component 212 is placed at a distal end 205 of cannula 104 while the proximal end 207 of cannula 104 is connected to a hand-piece (e.g., hand-piece 102 shown in FIG. 1A). As described above, distal end 205 of cannula 104 is the end that is inserted into the patient's body part, or where laser light is configured to be emitted out of probe assembly 100. Also, as shown, lens 210 comprises proximal end 209 and distal end 211. Further, protective component 212 comprises proximal end 215 and distal end 213.

In certain aspects, protective component 212 comprises an optically clear or transparent material. In certain aspects, the transparent material has optical power and, in certain other aspects, the transparent material does not have optical power. Optical power (also referred to as dioptric power, refractive power, focusing power, or convergence power) is the degree to which a lens, mirror, or other optical system converges or diverges light. In certain aspects, protective component 212 may comprise material that is able to tolerate high temperatures without melting. For example, protective component 212 may have a transition temperature in the range of 800° C. to 2000° C. Examples of the transparent material include Sapphire, fused silica, or other glass or ceramics materials with high transition temperatures.

In certain aspects, protective component 212 is attached to cannula 104 by way of press-fitting of component 212 into cannula 104. Press-fitting, also known as interference fitting or friction fitting, is a technique for securing protective component 212 to cannula 104, the securing being achieved by friction between protective component 212 and cannula 104 after protective component 212 is pushed into cannula 104. In certain aspects, cannula 104 comprises material such as stainless steel, Nitinol (NiTi), or a Platinum-iridium alloy (Pt-Ir). In certain aspects, protective component 212, comprises material with enough robustness or rigidity (e.g., hardness or toughness) such that press-fitting protective component 212 into cannula 104 would not result in fracturing protective component 212, especially when cannula 104 is also made of rigid material (e.g., stainless steel). In certain aspects, cannula 104 may have an internal diameter that is smaller than the diameter of protective component 212.

Figure 2B:
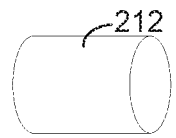
FIG. 2B illustrates a three-dimensional view of the protective component of FIG. 2A, according to some embodiments.

FIG. 2B illustrates a three-dimensional view of protective component 212. As shown, in certain aspects, protective component 212 is a cylindrical component that may be press-fitted into the cylindrical opening of cannula 104. In certain aspects, the diameter of protective component 212 may be 350 µm±5 µm, 360 µm±5 µm, or 370 µm±5 µm. In certain aspects, the length of protective component 212 may be as long as 355 µm±25 µm.

Figure 2C:
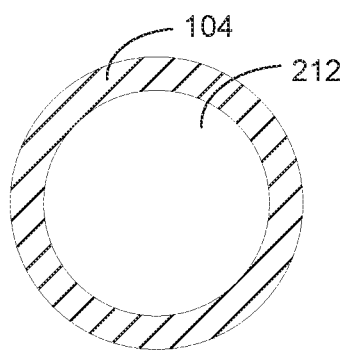
FIG. 2C illustrates a front view of the tip of the cannula shown in FIG. 2A, according to some embodiments.

FIG. 2C illustrates a front view of the tip of cannula 104 that houses protective component 212.

Figure 2D:
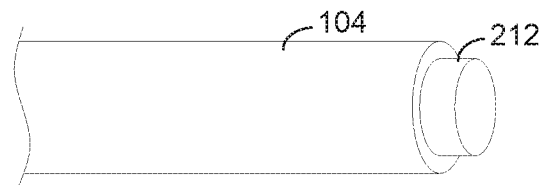
FIG. 2D illustrates a three-dimensional view of the tip of the cannula shown in FIG. 2A, according to some embodiments.

FIG. 2D illustrates a three-dimensional view of the tip of cannula 104. As shown, protective component 212 partially extends outside of cannula 104. Although, in certain aspects, protective component 212 does not extend outside of cannula 104. For example, protective component 212 may be flush with the outside of cannula 104, or not extend to the outside of cannula 104.

As shown in FIGS. 2A-2D, in certain aspects, a protective component (e.g., protective component 212) may have a cylindrical shape with distal and proximal ends that are both flat. However, in certain aspects, the proximal end of the protective component need not be flat. For example, the proximal end of the protective component may be spherical or aspheric. A protective component with a spherical or aspheric proximal end may be advantageous because a spherical or aspheric proximal end may be more easily guided or inserted through the tip of a cannula during press-fitting.

Also, as shown in FIG. 2A, in certain aspects, a lens (e.g., lens 210) placed in cannula 104 has a cylindrical shape with distal and proximal ends that are both flat. An example of such a lens is a gradient-index (GRIN) lens. However, in certain other aspects, a spherical or aspherical lens may be used instead, which may increase the performance and/or thermal reliability of the corresponding probe assembly. As such, in certain aspects, at least one of the proximal or distal ends of the lens is not flat. For example, the proximal, distal, or both ends of the lens may be spherical or aspherical. Note that, any of the different shapes of lenses described herein may be used in conjunction with any of the different shapes of protective components described herein.

FIGS. 3A-3E illustrate cross-sectional views of a number of example configurations of different shapes of lenses and protective components within cannula 104.

Figure 3A:
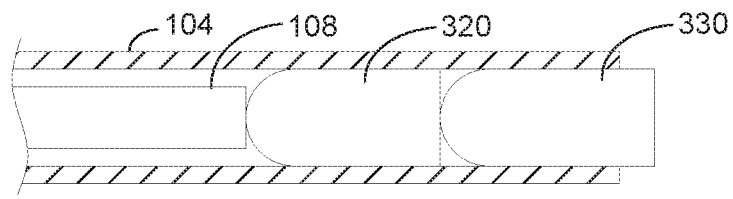
FIGS. 3A-3E illustrate cross-sectional views of a number of example configurations of different shapes of lenses and protective components, according to some embodiments.

FIG. 3A illustrates cannula 104 through which optical fibers 108 partially extend. As shown, at the distal end of optical fibers 108 is lens 320, with a proximal end that is spherical and a distal end that is flat. Protective component 330 is press-fitted into cannula 104 to be placed at the distal end of lens 320 in order to restrict lens 320 from movement along and detachment from cannula 104. The spherical proximal end of lens 320 steers the laser beams, which are propagated by optical fibers 108, towards the middle of the proximal end of protective component 330.

Figure 3B:
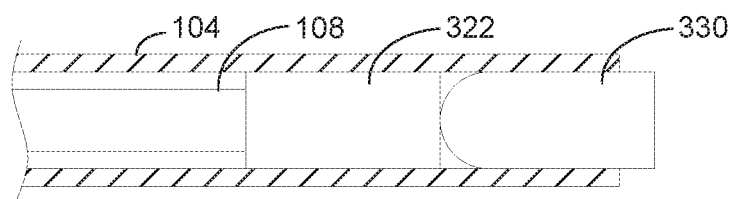

FIG. 3B illustrates protective component 330 protecting lens 322 with flat proximal and distal ends. In certain aspects, lens 322 is a GRIN lens.

Figure 3C:
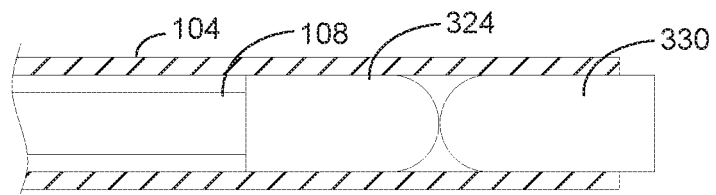

FIG. 3C illustrates protective component 330 protecting lens 324 with a proximal end that is flat and a distal end that is spherical. In certain aspects, there is an optical power split between the spherical distal end of lens 324 and the spherical proximal end of protective component 330, resulting in less spherical aberrations (e.g., more fidelity). Reducing the spherical aberrations results in the probe assembly projecting or propagating sharper laser spots on the patient's body part (e.g., retinal surface), which may improve the performance and accuracy of the probe assembly.

Figure 3D:
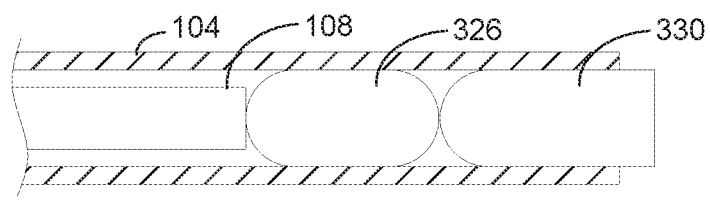

FIG. 3D illustrates protective component 330 protecting lens 326 with spherical proximal and distal ends. In certain aspects, lens 326 (e.g., referred to as a spherical lens) has a higher temperature performance than a GRIN lens. The protection provided by protective component 330 allows for the use of a spherical lens, such as lens 326. In certain aspects, spherical lens 326 is able to focus laser beams, which are propagated by optical fibers 108, towards the middle of the proximal end of protective component 330. In the example of FIG. 3D, the spherical end of protective component 330, in combination with the two spherical ends of lens 326, further helps with steering and focusing the laser beams. In addition, a high-softening-point spherical lens may be able to tolerate a higher surface temperature, which may improve the thermal reliability of the probe assembly.

Figure 3E:
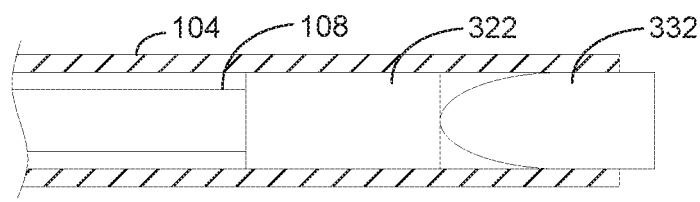

FIG. 3E illustrates protective component 332 protecting lens 322 with flat proximal and distal ends. Protective component 332 has a proximal end that is aspherical and a distal end that is flat. In certain aspects, the aspherical end of protective component 332 may be molded. In certain aspects, a protective component with an aspheric proximal end can be more easily guided or inserted through the tip of cannula 104 than a spherical proximal end.

As described above, in certain aspects, one or more of protective components 330-332 may possess optical power, while, in other aspects, the protective components may not have optical power. Also, in certain aspects, in each of the 3A-3E configuration, the distal end of the optical fibers touches or is proximate to the proximal end of the lens while the distal end of the lens touches or is proximate to the proximal end of the protective component. In such aspects, the lens's movement is restricted by the optical fibers from the one side (e.g., proximal side) and the protective component from the other side (e.g., distal side).

Figure 4A:
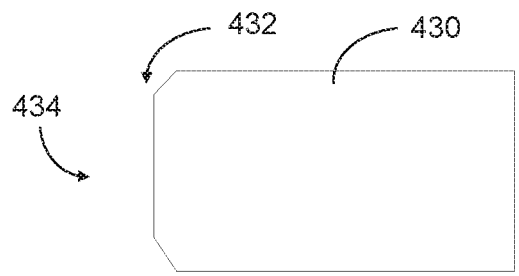
FIG. 4A illustrates a cross-sectional view of a protective component with a beveled end, according to some embodiments.
Figure 4B:
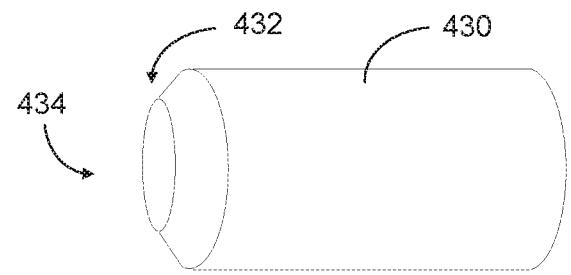
FIG. 4B illustrates a three-dimensional view of the protective component of FIG. 4A, according to some embodiments.

FIG. 4A illustrates a cross-sectional view of another example shape for a protective component. As shown, the proximal end of protective component 430 comprises beveled edges 432 and a flat surface 434. For example, protective component 430 may be manufactured by beveling the edges of the proximal end of a cylindrical component. FIG. 4B illustrates a three-dimensional view of protective component 430. Protective component 430 is advantageous because the bevel-shaped proximal end of protective component 430 can be more easily guided or inserted through the tip of a cannula.

Figure 4C:
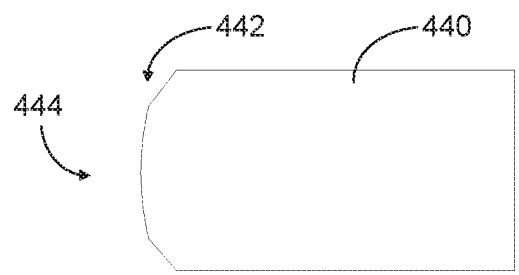
FIG. 4C illustrates a cross-sectional view of a protective component with a beveled end, according to some embodiments.
Figure 4D:
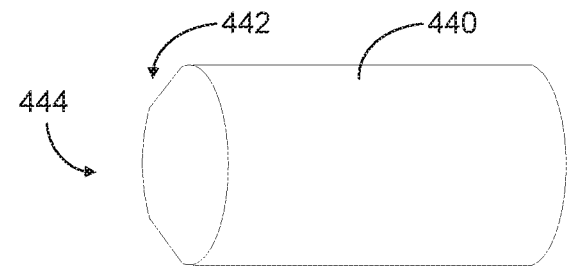
FIG. 4D illustrates a three-dimensional view of the protective component of FIG. 4C, according to some embodiments.

FIG. 4C illustrates a cross-sectional view of yet another example shape for a protective component. As shown, the proximal end of protective component 440 comprises beveled edges 442 and spherical surface 444. FIG. 4D illustrates a three-dimensional view of protective component 440.

A protective component, such as protective component 430 or 440, may be advantageous because the bevel-shaped proximal end of the protective component may be more easily guided or inserted through the tip of a cannula. Protective components 430 or 440 may be used in conjunction with any of the lens configurations 320-326 shown in FIGS. 3A-3E.

In certain aspects, a cannula (e.g., cannula 104) may be made from flexible material (e.g., stainless steel, NiTi, Pt-lr, etc.) such that the diameter of the cannula may expand when a lens and/or a protective component with a larger diameter is inserted into the cannula.

Figure 4E:
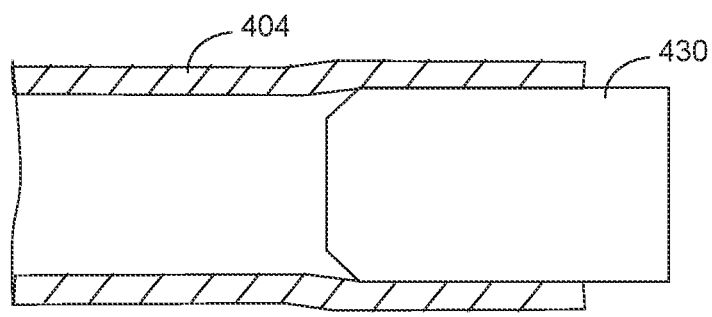
FIG. 4E illustrates the protective component of FIG. 4A being inserted into a cannula, according to some embodiments.

FIG. 4E illustrates protective component 430 of FIG. 4A being inserted into a cannula (e.g., cannula 404). As shown, the diameter of the tip of the cannula has expanded and taken the shape of the beveled end of protective component 430. In certain aspects, using a protective component with a diameter that is larger than the diameter of the cannula in its normal state is advantageous. This is because, in such aspects, press-fitting the protective component into the cannula eliminates, minimizes, or, at least, reduces any unfilled space or opening between the outer surface of the protective component and the inner surface of the cannula. As a result, any possibility of fluids, such as blood, leaking into the cannula through any such unfilled spaces or openings may also be reduced.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A probe assembly, comprising:
    a multi-core optical fiber;
    a nitinol cannula, wherein the multi-core optical fiber extends at least partially through the nitinol cannula for transmitting laser light from a laser source to a target location;
    a gradient index (GRIN) lens housed in the cannula, wherein the multi-core optical fiber touches a proximal end of the GRIN lens; and
    a cylindrical sapphire window press-fitted to a distal end of the nitinol cannula, wherein a distal end of the GRIN lens touches a proximal end of the cylindrical sapphire window inside the nitinol cannula and wherein a distal end of the cylindrical sapphire window extends outside the nitinol cannula, wherein the GRIN lens is positioned between the multi-core optical fiber and the cylindrical sapphire window and wherein the GRIN lens is external to the cylindrical sapphire window.

2. The probe assembly of claim 1, wherein the cylindrical sapphire window comprises transparent material.

3. The probe assembly of claim 2, wherein the cylindrical sapphire window has optical power.

4. The probe assembly of claim 2, wherein the cylindrical sapphire window is without optical power.

5. The probe assembly of claim 1, wherein the proximal end of the cylindrical sapphire window comprises a convex surface.

6. The probe assembly of claim 1, wherein the proximal end of the cylindrical sapphire window comprises a spherical segment.

7. The probe assembly of claim 1, wherein the proximal end of the cylindrical sapphire window comprises a molded aspherical segment.

8. The probe assembly of claim 1, wherein the proximal end of the GRIN lens is curved.

9. The probe assembly of claim 8, wherein the proximal end of the GRIN lens is spherical.

10. The probe assembly of claim 1, wherein the distal end of the GRIN lens is curved.

11. The probe assembly of claim 10, wherein the proximal end of the GRIN lens is spherical.

12. The probe assembly of claim 1, wherein the cylindrical sapphire window is press-fitted such that the cylindrical sapphire window reduces leakage of material into the nitinol cannula.

13. A surgical system, comprising:
a laser source;
a multi-core optical fiber;
a probe assembly connected to the laser source through the multi-core optical fiber, the probe assembly comprising:
a hand-piece connected to a nitinol cannula, the nitinol cannula comprising a distal end, wherein the multi-core optical fiber extends through the hand-piece and at least partially through the nitinol cannula for transmitting laser light from the laser source to a target location;
a GRIN lens housed in the cannula, wherein the multi-core optical fiber touches a proximal end of the GRIN lens; and
a cylindrical sapphire window press-fitted to the distal end of the nitinol cannula, wherein a distal end of the GRIN lens touches a proximal end of the cylindrical sapphire window inside the nitinol cannula and wherein a distal end of the cylindrical sapphire window extends outside the nitinol cannula, wherein the GRIN lens is positioned between the multi-core optical fiber and the cylindrical sapphire window and wherein the GRIN lens is external to the cylindrical sapphire window.

14. The surgical system of claim 13, wherein the cylindrical sapphire window comprises transparent material.

15. The surgical system of claim 14, wherein the cylindrical sapphire window has optical power.

16. The surgical system of claim 14, wherein the cylindrical sapphire window is without optical power.

17. The surgical system of claim 13, wherein the proximal end of the cylindrical sapphire window comprises a convex surface.

18. The surgical system of claim 13, wherein the proximal end of the cylindrical sapphire window comprises a spherical segment.

19. The surgical system of claim 13, wherein the proximal end of the cylindrical sapphire window comprises a molded aspherical segment.

20. The surgical system of claim 13, wherein the cylindrical sapphire window is press-fitted such that the cylindrical sapphire window reduces leakage of material into the nitinol cannula.

* * * * *